United States Patent [19]
Pratt

[11] Patent Number: 5,369,032
[45] Date of Patent: Nov. 29, 1994

[54] APPARATUS FOR ADMINISTERING LIVE BACTERIA AS FEED ADDITIVES TO LIVESTOCK AND POULTRY

[75] Inventor: William C. Pratt, Canyon, Tex.

[73] Assignee: Micro Chemical, Inc., Amarillo, Tex.

[21] Appl. No.: 161,201

[22] Filed: Dec. 2, 1993

Related U.S. Application Data

[60] Continuation of Ser. No. 486,952, Mar. 1, 1990, abandoned, which is a division of Ser. No. 215,210, Jul. 5, 1988, Pat. No. 4,910,024.

[51] Int. Cl.$^5$ .............................................. C12M 1/38
[52] U.S. Cl. ..................................... 435/290; 435/289; 435/316; 435/260; 222/77; 222/58; 366/141; 366/144; 366/145; 366/147; 366/149
[58] Field of Search ............... 435/284, 286, 287, 289, 435/290, 291, 302, 305, 316, 813, 260; 366/144, 145, 147, 148, 141, 149; 222/77, 65, 66, 23, 58; 141/83

[56] References Cited

U.S. PATENT DOCUMENTS

| | | | |
|---|---|---|---|
| 2,448,927 | 5/1942 | Fischer | 366/144 |
| 3,039,936 | 6/1962 | McLimans | 435/286 |
| 3,437,075 | 4/1969 | Hawes, Jr. et al. | 222/2 |
| 3,498,311 | 3/1970 | Hawes, Jr. | 222/2 |
| 3,670,923 | 6/1972 | Hawes et al. | 222/2 |
| 3,713,836 | 1/1973 | Carlsson . | |
| 3,806,001 | 4/1974 | Pratt | 222/132 |
| 3,822,056 | 7/1974 | Hawes et al. | 259/25 |
| 3,924,007 | 12/1975 | Driessen et al. | 426/43 |
| 3,946,657 | 3/1976 | Driessen et al. | 99/455 |
| 3,953,609 | 4/1976 | Farr | 426/2 |
| 3,984,286 | 10/1976 | Malick | 195/141 |
| 3,985,622 | 10/1976 | Hawkins | 195/142 |
| 4,019,962 | 4/1977 | Allen et al. | 435/316 |
| 4,036,699 | 7/1977 | Quigg | 195/142 |
| 4,048,473 | 9/1977 | Burkhart | 366/145 |
| 4,055,666 | 10/1977 | Jeffreys et al. | 426/31 |
| 4,073,696 | 2/1978 | Müller | 435/311 |
| 4,115,199 | 9/1978 | Porubcan et al. | 195/96 |
| 4,212,950 | 7/1980 | Adams | 436/316 |
| 4,276,384 | 6/1981 | Mueller | 435/311 |
| 4,379,846 | 4/1983 | Shkidchenko et al. | 435/316 |
| 4,502,416 | 3/1985 | Keysell et al. | 366/145 |
| 4,518,696 | 5/1985 | Gehrman et al. . | |
| 4,521,434 | 6/1985 | Matrozza | 426/59 |
| 4,657,762 | 4/1987 | Mikkola et al. | 424/93 |
| 4,670,397 | 6/1987 | Wegner et al. | 435/289 |
| 4,689,226 | 8/1987 | Nurmi et al. | 424/93 |
| 4,733,971 | 3/1988 | Pratt | 366/141 |
| 4,797,289 | 1/1989 | Reddy | 426/43 |

(List continued on next page.)

OTHER PUBLICATIONS

Cobactin ® Label, BioTechniques Laboratories Inc.
Cobactin ® Directions for Use (20-, 100-, and 500-dose packages).

(List continued on next page.)

Primary Examiner—James C. Housel
Assistant Examiner—Long V. Le
Attorney, Agent, or Firm—Klarquist Sparkman Campbell Leigh & Whinston

[57] ABSTRACT

An apparatus for preparing at a livestock feedlot a concentrated suspension of anaerobic bacteria at a known, accurate concentration and for storing the prepared suspension for prolonged periods at the feedlot in a ready-to-use condition without significant loss of viability, allowing feedlot operators to conveniently administer such bacterial supplements to large numbers of livestock as a probiotic on a regular basis in accurate dosages. The apparatus comprises an insulated liquid-holding vessel cooled by refrigeration appliance, and mixing and recirculation appliances to ensure temperature and concentration homogeneity of the bacterial suspension. The vessel and contents are gravimetrically monitored to ensure accuracy of bacterial concentration. In each of several embodiments, at time of intended use, a preselected mass or volume of bacterial liquid suspension is dispensed on demand from the vessel into a separate mixing tank for further accurate dilution and for addition of other microingredients to the suspension, as required, immediately before adding to and mixing with a known mass or volume of animal feed. The apparatus can be used with or without a separate microingredient weighing or volumetric metering system.

12 Claims, 2 Drawing Sheets

U.S. PATENT DOCUMENTS

| | | | |
|---|---|---|---|
| 4,806,368 | 2/1989 | Reddy | 426/61 |
| 4,815,042 | 3/1989 | Pratt | 366/141 |
| 4,840,905 | 6/1989 | Kearns et al. | 435/286 |
| 4,883,759 | 11/1989 | Hopkins | 435/289 |
| 4,980,164 | 12/1990 | Manfredi et al. | 424/93 |

OTHER PUBLICATIONS

Shahani et al., "Role of Dietary Lactobacilli in Gastrointestinal Microecology," *Am. J. Clin. Nutri.* 33:2448–2457 (1980).

Savaiano et al., "Lactose Maladsorption from Yogurt, Pasteurized Yogurt, Sweet Acidophilus Milk, and Cultured Milk in Lactose-Deficient Individuals," *Am. J. Clin. Nutri.* 40:1219–1223 (1984).

Patching et al., "The Effects and Control of Temperature," in Norris et al. (eds.) *Methods in Microbiology*, vol. 2, Chapter II, Academic Press (1970).

Smith, *Biotechnology Principles (Aspects of Microbiology 11)*, Chapter 3, Van Nostrand Reinhold (1985).

Robinson et al., *Yoghurt Science and Technology*, Chapter 8, Pergamon (1985).

Cherry-Burrell Corp. product literature (1990).

Cobactin ® product literature, BioTechniques Laboratories, Inc.

Cole et al., "Influence of Realimentation Diet on Recovery of Rumen Activity and Feed Uptake in Beef Steers," *J. Animal Sci.* 61:692–701 (1985).

DCI, Inc., product literature.

Paul Mueller Co. product literature.

Exhibit 1 – Declaration of William C. Pratt.

Exhibit 2 – Copy of Declaration of Eugene T. Manfredi.

Klaenhammer, T. R., "Microbiological Considerations in Selection and Preparation of Lactobacillus Strains for Use as Dietary Adjuncts," *J. Dairy Sci.* 65:1339–1349 (1982).

Gedek, B., "Probiotics in Animal Feeding – Effects on Performance and Animal Health," *Feed Magazine* (Nov., 1987).

Cobactin Unit Operator's and Service Manual, Micro Chemical, Inc., Feb. 1988.

APPARATUS FOR ADMINISTERING LIVE BACTERIA AS FEED ADDITIVES TO LIVESTOCK AND POULTRY

CROSS REFERENCE TO RELATED APPLICATION

This application is a continuation of application Ser. No. 07/486,952, filed on Mar. 1, 1990, now abandoned, which application is a division of U.S. patent application Ser. No. 07/215,210, filed on Jul. 5, 1988, now U.S. Pat. No. 4,910,024.

BACKGROUND OF THE INVENTION

1. Field of the Invention

The present invention relates to the administering of live, probiotic anaerobic bacteria to livestock. More particularly, it relates to a method and apparatus for preparing, containing and preserving the viability of an aqueous suspension of said bacteria as a concentrated, homogeneous suspension under controlled-temperature conditions at a feedlot location until time for addition of a diluted portion thereof to animal feed, whereby said bacteria can be regularly administered to large numbers of animals in an efficient manner.

2. General Discussion of the Background

It has long been a common practice to administer chemical additives to cattle and other livestock to supplement feed rations, thereby providing a balanced diet, protecting the animals from disease, and stimulating growth. Such additive supplements, commonly termed microingredients, usually should be administered to each animal on a regular basis in carefully controlled dosages to ensure optimal benefit. Individual dosages are typically small due to the high potency of microingredients.

A number of methods and apparatuses have been devised for accurately dispensing, at the feedlot, separately stored livestock feed additive chemical concentrates into a volume of fluent carrier material, such as water, for dilution, dispersion, and suspension, and for transporting the resulting slurry into livestock drinking water or feed rations shortly before the time of intended consumption. These methods and apparatuses are disclosed in U.S. Pat. Nos. 3,437,075; 3,498,311; 3,670,923; 3,806,001; 3,822,056; and 4,733,971, the disclosures of which are incorporated herein by reference.

Additive supplements can also include specific live microorganisms. For example, administration of certain live probiotic bacteria can help restore optimal intestinal flora in animals such as cattle, especially after stressful situations such as transport to a feedlot. Gedek, B., "Probiotics in Animal Feeding—Effects on Performance and Animal Health," *Feed Magazine*, Nov., 1987. With regular administration, probiotic bacteria also increase nutrient absorption efficiency and help control the proliferation of harmful microorganisms in the animals' digestive tracts that could otherwise cause disease conditions adversely affecting rates of animal development and weight gain. A bacterial species commonly administered to cattle for such purposes is *Lactobacillus acidophilus*, an anaerobic, lactic acid producer. Klaenhammer, T. R. (1982) "Microbiological Considerations in Selection and Preparation of Lactobacillus Strains for Use as Dietary Adjuncts," *J. Dairy Sci.* 65: 1339–1349. An example of such a product is "Cobactin," a lyophilized *L. acidophilus* formulation from Biotechniques Laboratories, Inc., Redmond, Wash.

Anaerobic bacteria are adversely sensitive to environmental influences such as oxygen, moisture, temperature extremes, and many chemicals. Until recently, the bacteria were mixed with dry, diluting filler material and other additive supplements as a premix. However, animal weight-gain results obtained with such bacteria-containing premixes were inconsistent because large numbers of bacteria died in the premix before addition to feed due to improper formulation, packaging and storage of the premix. At least one manufacturer of bacterial supplements has partially overcome these problems by lyophilizing the bacteria in the absence of chemical microingredients and packaging the dry bacteria in hermetically sealed packets under an inert, arid atmosphere such as dry nitrogen. These advances greatly extend the shelf-life of commerically packaged anaerobic bacterial formulations. However, even properly packaged anaerobic bacteria become labile due to contact with air and moisture the moment the package is opened. Therefore, such packaging still does not solve the problem of maintaining the bacteria in a live state and delivering them to large numbers of animals in proper dosages after the package is opened. Without some means of extending viability, anaerobic bacteria from an opened package must be properly diluted and presented to the animals within a very short time after opening the package, which is time prohibitive and impractical in large feedlots. Hence, there is still a need for a method and apparatus for preserving bacteria, after opening the package, in a ready-to-use viable condition at a known concentration that can be delivered at the correct dosages efficiently on a regular basis to large numbers of animals.

There are several known methods used to administer bacteria from a dry concentrate to animals, but the existing methods have significant drawbacks. One known method is to rehydrate the dry bacteria in dilute aqueous suspension and administer the suspension orally via drenching. However, drenching is so cumbersome and time-prohibitive that it is usually only performed during times of critical need, such as immediately after the animals arrive at the feedlot or when an animal is obviously sick.

A second known method is to manually sprinkle dried bacteria onto animal feed in the feed bunks, which is time-prohibitive in large feedlots. Also, to attain more uniform distribution, appreciable predilution of the concentrated bacteria with dry filler material is required, which causes appreciable loss of bacterial viability resulting from contact with concentrated substances. Furthermore, it is practically impossible via this method to ensure that each animal receives a correct and consistent dose when many animals feed from the same bunk.

A third known method is to mix the dry bacteria with feed before distribution to the feed bunks. This method is undesirable because homogeneity of such a mixture is very difficult to attain and because large numbers of bacteria are killed by the time the mixture is presented to the animals.

Accordingly, there remains no known practical method or apparatus for accurately administering regular, small dosages of probiotic bacteria to livestock on a large scale, despite the need for such a method and apparatus.

Heretofore, the aforementioned methods and apparatuses for regularly administering chemical microingredients in small, accurate dosages to livestock on a large scale in a liquid carrier slurry through their feed rations have been thought to be inapplicable to live, anaerobic bacteria of the class described because of the lack of any method or means for storing the bacterial additive in a form that would maintain the viability of the bacteria and yet be usable in such prior methods and apparatuses. More specifically, to be applicable to such prior methods and apparatuses, the live bacteria would need to be stored for prolonged periods of time in dry particulate or liquid form in a known, constant concentration at a feedlot for immediate dispensing by weight or volume, on demand. As a result, despite general knowledge of the benefits of regular administration of probiotics to certain livestock, feedlot operators have not done so because of inadequate methods and lack of a suitable apparatus.

Hence, there is a need for a method and apparatus for: (a) preparing and storing at the feedlot a homogeneous volume of bacterial material, at known concentration and ready for on-demand use, where the bacteria are preserved in a viable state until immediately before presentation to the animals and in a form conducive to accurate dispensing by weight or volume; and (b) feeding the bacteria in a live condition to large numbers of livestock on a regular basis such that each animal receives a correct dosage of live bacteria, preferably mixed with its feed, and with other microingredients as required.

Accordingly, a primary object of the present invention is to provide a method and apparatus for delivering a known dosage of desired live bacteria mixed with animal feed to large numbers of livestock for ingestion on a regular basis.

Another primary object is to provide a method and apparatus for preserving and storing at a feedlot location a known concentration of a liquid suspension of desired bacteria in live form for prolonged periods in a condition for immediate, on-demand use for administration to animals.

Another primary object is to provide a method and compact apparatus for preparing and storing a concentrated volume of aqueous liquid suspension of live, probiotic bacteria at known concentration at an animal feedlot location, and for preserving said bacteria in a viable condition at a known, stable concentration until time for adding a known mass or volume thereof to animal feed.

Another primary object is to provide a method and apparatus as aforesaid for preparing and storing a concentrated volume of aqueous, liquid suspension of live probiotic bacteria and for preserving said bacteria in a viable condition at a known, stable concentration until time for removing a known mass or volume thereof for further dilution and addition of other microingredients before adding to a known mass or volume of animal feed. Another primary object is to provide a method and apparatus for delivering said concentrated bacterial liquid suspension to a gravimetric or volumetric measuring device to accurately dispense a preselected mass or volume, respectively, of the concentrated bacterial liquid suspension to a known mass or volume of aqueous liquid containing other microingredient additives, which is subsequently added to a known mass of livestock feed ration just before the feed ration is presented to the animals for consumption.

Another primary object is to provide a method and apparatus for preparing and storing a concentrated volume of aqueous, liquid suspension of live probiotic bacteria and for preserving said bacteria in a viable condition at a known, stable concentration until time for removing a known mass or volume thereof for further dilution and addition of other microingredients before therapeutically administering to animals via other methods such as drenching.

Another primary object is to provide a method and apparatus as aforesaid that adjust the temperature of the concentrated bacterial liquid suspension to within a preselected range for optimal bacterial survival in a viable condition at a known, stable concentration and regulate said temperature within that range uniformly throughout the volume of concentrated bacterial liquid suspension.

Another primary object is to provide a method and apparatus that insulate the concentrated bacterial liquid suspension contained within said apparatus from changes in ambient temperature.

Another primary object is to provide a method and apparatus as aforesaid that keep the concentrated bacterial liquid suspension contained therein uniform with respect to concentration of bacteria

SUMMARY OF THE INVENTION

The aforementioned objects are achieved by a storage and preservation method and apparatus for preparing and containing at the feedlot a volume of concentrated bacterial liquid suspension in a known concentration and preserving the suspended live bacteria in a viable state under controlled conditions until time for adding a known mass or volume thereof to animal feed. The bacteria are typically of a strain conferring a probiotic benefit to the type and breed of livestock that will ingest the bacteria, and are administered in precise live dosages to the livestock for an increased rate of weight gain, enhanced resistance to disease, and other beneficial purposes. The concentrated liquid suspension of bacteria is controllably delivered from the storage apparatus to a gravimetric or volumetric measuring device (such as that disclosed in my U.S. Pat. No. 4,733,971) where the suspension is controllably dispensed, metered or weighed, and subsequently delivered at predetermined rates or weights to and mixed homogeneously with a liquid aqueous carrier into which other dry particulate and liquid additive concentrates may also be delivered in predetermined quantities and concentrations. The resulting dilute suspension is then delivered into and mixed with feed ration shortly before presentation to the animals for consumption.

The present invention makes possible for the first time the simultaneous administration of accurate dosages of live bacteria to large numbers of livestock animals on a regular basis for probiotic, therapeutic, or other purposes. Heretofore, there has been no practical method or means to prepare at the feedlot a suspension of live bacteria prior to time of anticipated use and to maintain the viability of the bacteria while in a ready-to-use state.

In a preferred embodiment as shown and described, the desired volume of concentrated bacterial liquid suspension is contained in a thermally insulated vessel. A gravimetric scale or other weigh means monitors the combined weight of the vessel and its liquid contents, and ensures that the vessel is filled precisely with a preselected mass of aqueous carrier medium. A refrigeration means cools the bacterial liquid suspension to within a desired range, and maintains the temperature thereof within that range. An electronically controlled mixing means agitates the bacterial liquid suspension contained in the vessel to facilitate dispersion of bacteria in the aqueous carrier medium and to maintain temperature uniformity. The apparatus includes an electronically controlled means for recirculating the bacterial liquid suspension to maintain temperature and concentration homogeneity of the concentrated bacterial liquid suspension contained in the vessel and plumbing connected thereto. The vessel is covered to prevent environmental contamination of the contents and to restrict air circulation. The cover has a smaller hinged access door to allow filling of the vessel with aqueous carrier medium and for adding a fresh supply of dry bacteria. Finally, the apparatus also includes a means for controllably dispensing a volume of concentrated bacterial liquid suspension from the vessel to a separate weighing or volumetric measuring means for further controlled dilution of the concentrated bacterial liquid suspension and optional intermixing with other additives in a predetermined formulation before addition of the same to animal feed.

Volumetric or gravimetric dispensing of concentrated bacterial liquid suspension from the vessel to a hopper or slurry mixing vessel in the separate metering or weighing system is controlled by a central processing unit. The central processing unit is also electronically interfaced with the separate weighing system according to U.S. Pat. No. 4,733,971, which is incorporated herein by reference.

BRIEF DESCRIPTION OF THE DRAWINGS

The above and other objects and advantages of the present invention will become more apparent from the following detailed description of a presently preferred embodiment, which proceeds with reference to the accompanying drawings wherein.

DETAILED DESCRIPTION OF THE PREFERRED EMBODIMENTS

The present invention is a novel method and apparatus for preparing and storing a concentrated liquid suspension of anaerobic bacteria for use as a probiotic that can be accurately administered in regular, small dosages to livestock on a large scale at a feedlot. In the preferred embodiments, the bacteria are suspended in an aqueous carrier medium having minimal nutrient content to prevent growth or multiplication of the bacteria while still sustaining viability of the organisms. The temperature of the suspension is maintained sufficiently low to inhibit anabolic or catabolic processes that degrade viability (generally, between 36° F. to 50° F.). The suspension is kept homogeneous with respect to concentration of bacteria and uniform in temperature. The volume of stored bacterial liquid suspension is kept small to avoid the necessity for large, bulky equipment while containing an adequate supply of ready-to-use bacteria. For example, a 400-gram packet of dried bacteria, when added to only ten pounds of water, yields a quantity of bacteria in concentrated suspension sufficient to dose 10,000 head of cattle at a single feeding. Also, the apparatus is locatable at a feedlot where feed batches can be formulated and prepared immediately before distribution to the animals. Finally, the apparatus of the present invention is usable in conjunction with existing apparatuses that perform an accurate second dilution step just before adding the bacteria to the feed. For example, in U.S. Pat. No. 4,733,971, I describe an apparatus wherewith known masses or volumes of chemical additives in liquid or dry form are suspended in a known mass or volume of carrier liquid such as water before addition to animal feed. Addition of a known mass of concentrated bacterial suspension from the apparatus of the present invention to the volume of suspension prepared by the apparatus of my aforesaid patent would achieve sufficient secondary dilution.

General Assembly

Figure 1:
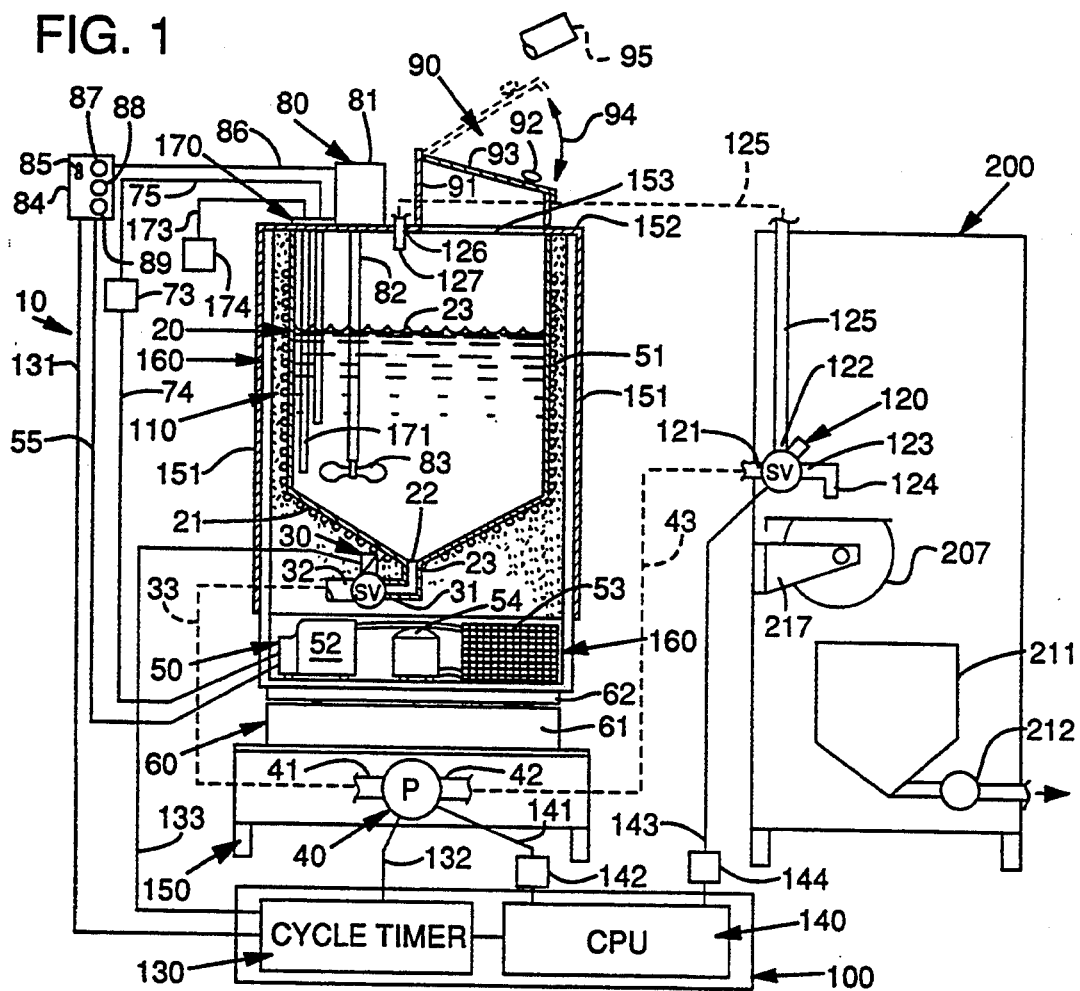
FIG. 1 is a side elevational view diagrammatically depicting the major components of an apparatus in accordance with the present invention.

With reference to the drawings, FIG. 1 illustrates an apparatus shown generally at 10 for preparing, storing, and preserving a volume of known concentration of a concentrated, aqueous suspension of live bacteria to be used as a daily probiotic supplement for livestock. Apparatus 10 comprises a number of major components, including a liquid-holding means or vessel 20 with access means 90; an agitating means including an electrically driven mixer 80, electrically driven pump 40, and electrically actuated valve 30; a temperature control means including a thermostat means 70, refrigeration means 50, and insulation means 110; a weighing means 60; a liquid-level detection means 170; and a delivery means including an electrically driven pump 40, electrically actuated valves 30 and 120, and control means 100. Control means 100 includes a central processing unit (CPU) 140 and cycle timer 130.

Frame and Subframe

Referring further to FIG. 1, apparatus 10 comprises basically two frame structures: subframe 150 and frame 160, together with components supported thereby. Subframe 150 is situated beneath frame 160 and supports pump 40 and weighing means 60, the latter comprising generally gravimetric scale 61 which measures the weight of objects resting on its loading pan 62. Frame 160 rests directly on loading pan 62 and supports generally refrigeration means 50, vessel 20, valve 30, exterior side panels 151, top cover 152, access means 90, mixer 80, thermostat means 70, liquid-level detection means 170, insulation 110, cycle timer 130, and motor speed controller 84.

Liquid-Holding Vessel and Surrounding Components

Vessel 20 is typically cylindrical with its lower end 21 shaped like an inverted cone to facilitate complete draining of liquid contained therein. Vessel 20 is typically constructed of stainless steel. However, it may be made from any other suitable material that does not corrode, contribute toxic substances to contacting aqueous liquids, or deteriorate from prolonged contact with aqueous solutions of the types anticipated during use, and that has acceptable thermal and mechanical characteristics. The volume of vessel 20 is preferably within the range of three to five gallons, but other capacities are also possible and are within the scope of the present invention.

Vessel 20 is mounted vertically inside and at the uppermost portion of frame 160, with the conical portion 21 pointed downward. The apex of conical portion 21 has a round opening 22 to which is connected pipe elbow 23. The upper end of vessel 20 is covered with horizontal panel or cover 152 which has opening 153 externally enclosed by access means 90. Helically wrapped around the exterior of vessel 20 are evaporator coils 51 which comprise part of refrigeration means 50. In the preferred embodiment, the evaporator coils are in intimate contact with the exterior wall of vessel 20, such as by brazing or other suitable process. Insulation means 110, which may be liquid or suitable solid material, surrounds vessel 20 and evaporator coils 51. Exterior side panels 151, attached to appropriate members of frame 160, together with cover 152 and access means 90, complete the encapsulation of vessel 20.

Access means 90 comprises vertical panels 91, hinged lid 93, and handle 92. Hinged lid 93 normally remains in the closed position. Hinged lid 93 may be opened (94) to gain access to the interior of vessel 20 for adding a fresh supply of aqueous carrier liquid or of dried bacteria from a commercial packet 95, or for cleaning or inspecting the interior or contents 23 of vessel 20.

Mixer

Mixer 80 comprises electrically driven motor 81 mounted vertically atop cover 152, shaft 82 rigidly attached axially to the rotor of motor 81, mixing blade 83 rigidly attached to the distal end of shaft 82, and electronic motor speed control 84 electrically connected via cable 86 to motor 81. Shaft 82 is sufficiently long to ensure that mixing blade 83 is submerged whenever a threshold volume of liquid is contained in vessel 20.

Electronic motor speed controller 84 includes controls 87, 88 and 89 for adjusting various present angular velocities of mixing blade 83, as driven by motor 81, and manual control switch 85 for turning motor 81 on to rotate mixing blade 83 continuously at a particular preset angular velocity, as required. Motor speed controller 84 is also electrically interconnected with refrigeration means 50 (and thermostat means 70) via cable 55.

Weigh Means

Weighing means 60 is comprised generally of an electronic or mechanical gravimetric scale 61 mounted to the upper surface of subframe 150. (An electronic scale employing an electronic load cell for mass sensing may be less sensitive to environmental interferences such as liquid spills, dust, and mechanical vibration and shock, as well as more reliable, than mechanical beam-type or other scale means. However, either type will suffice.) Weighing means 60 may include a means by which the operator can input various gravimetric data such as "zeroing" the tare weight of that portion of apparatus 10 supported by scale 61, and setpoints corresponding to an "empty" or "full" status of vessel 20.

Temperature Control Means

The temperature control means is comprised generally of refrigeration means 50, thermostat means 70, and insulating means 110.

Refrigeration means 50 is of conventional design. It is mounted to frame 160, beneath vessel 20. Refrigeration means 50 consists generally of a compressor 52, condensor 53, receiver tank 54, and other necessary components. It includes evaporator coils 51 wrapped helically around the exterior of vessel 20. Evaporator coils 51 are filled with a suitable refrigerant and are appropriately hydraulically connected to compressor 52, condensor 53, receiver tank 54, and other components of refrigeration means 50.

Insulation means 110 in the preferred embodiment is comprised of any material suitable for use as a thermal insulator of vessel 20 and its contents 23, such as fibrous or foam material, when appropriately applied circumferentially around vessel 20 and evaporator coils 51.

In a second embodiment (not shown), insulation means 110 comprises a sealed, fluid-filled space between the exterior wall of vessel 20 and a second, wall-forming sheet of similar material conforming to the outside wall of vessel 20 and enclosing evaporator coils 51. In such a second embodiment, the space between the outside wall of vessel 20 and the inside wall of the conforming sheet is filled with a thermally absorptive liquid material such as propylene glycol. The evaporator coils in this second embodiment may be either in intimate contact with the outside wall of vessel 20 or suspended freely within said fluid-filled space. The outside wall of the conforming sheet may optionally be blanketed with fibrous or foam material as in the preferred embodiment for additional thermal insulation.

Thermostat means 70, mounted to cover 152, comprises a sealed probe 71 which extends vertically downward through an opening in cover 152 into vessel 20 such that the distal end of probe 71 is immersed in the liquid contents 23 of vessel 20 at an appropriate depth. Inside sealed probe 71 is a temperature-sensing element (not shown). An electrical switch 73 with appropriate supporting electronic circuitry is electrically connected to thermostat means 70 via cable 75, and to refrigeration means 50 via cable 74. Electrical switch 73 is mounted to frame 160.

Liquid Level Detection Means

Liquid level detection means 170, mounted to cover 152, comprises a probe 171 extending vertically downward through an opening in cover 152 into vessel 20 such that the distal end of probe 171 is immersed in the liquid contents 23 of vessel 20 at an appropriate depth. Inside probe 171 is any suitable switching device 172 that actuates when in contact with a contiguous volume of liquid, such as a conductivity cell, float switch, tilt switch, photo-optical device, or other suitable device that will trigger an electrical signal whenever the volume of liquid 23 in vessel 20 drops below a certain minimum level. Liquid level detection means 170 is electrically connected to alarm 174 via cable 173. Alarm 174 can be audio, visual, or other suitable alarm means, or a combination thereof.

Hydraulic Interconnection

Apparatus 10 is hydraulically plumbed as follows: Elbow 23 is connected to opening 22 on the bottom of vessel 20. The "IN" port 31 of electrically actuated, two-way, normally closed valve 30 is connected to the distal opening of elbow 23. (Valve 30 is preferably a solenoid valve, but other types of electrically actuated valves can also be used.) The "OUT" port 32 of valve 30 is connected via flexible hydraulic conduit 33 to the "IN" port 41 of electrically actuated pump 40 mounted to subframe 150. The "OUT" port 42 of pump 40 is connected via flexible hydraulic conduit 43 to the "IN" port 121 of electrically actuated three-way valve 120. (Valve 120 is preferably a solenoid valve, but other types of electrically actuated valves can also be used.) Valve 120 is mounted to a separate weighing or metering system 200 (such as described in my U.S. Pat. No. 4,733,971). To the normally closed "OUT" port 123 of valve 120 is attached an outlet nozzle 124 through which a dispensed volume of concentrated bacterial liquid suspension passes prior to further dilution, possible admixture with other microchemical additives, and admixture with animal feed. Flexible hydraulic conduit 125 is connected to normally open bypass port 122 of valve 120. The distal end of flexible hydraulic conduit 125 is connected to outlet nozzle 127, which passes vertically through cover 152 at opening 126.

Control Means

Cycle timer 130 is any suitable electrically-driven clock or timer-switch mounted to frame 160. It is electrically connected to pump 40 via cable 132, to valve 30 via cable 133, and to electronic motor speed controller 84 via cable 131. Cycle timer 130 comprises a sufficient number and type of relays or similar switching means actuated by an internal programmable clock-timer to turn on and off valve 30, pump 40 and motor 81.

Central processing unit (CPU) 140 is any suitable programmable microcomputer with keyboard and display, typically mounted separately from apparatus 10. CPU 140 is electrically connected to pump 40 via pump driven circuit 142 and cable 141 and to valve 120 via valve drive circuit 144 and cable 143. Pump drive circuit 142 and valve drive circuit 144 are suitable electronic switching devices that, upon receiving a logic signal from CPU 140, deliver sufficient electrical current at proper voltage to operate pump 40 and valve 120, respectively. CPU 140 is typically employed when apparatus 10 is used together with separate weighing and metering means 200, such as that in U.S. Pat. No. 4,733,971, where CPU 140 is the same device as shown as item 20. When apparatus 10 is used alone, functions performed by CPU 140 can alternatively be performed by a cycle timer or process controller. However, CPU 140 can also be used in the latter instance for monitoring mass measurements determined by scale 61, allowing the operator to "key in" a desired mass of bacterial liquid suspension to be dispensed from vessel 20 (represented by a loss of mass as measured by scale 61 during dispensation) and allowing CPU 140 to automatically control the actuation of valves and pump until precisely the desired mass is dispensed.

Operation

Vessel 20 contains the volume of concentrated bacterial liquid suspension 23 during preparation and storage thereof. In one embodiment, filling vessel 20 is accomplished by opening hinged door 93 and pouring in the desired mass of aqueous carrier medium, such as water, as measured by gravimetric scale 61. The contents of a commercial package 95 of lyophilized bacteria of the desired strain are added to the liquid in vessel 20. After filling, hinged door 93 is kept in the closed position. For example, a 400-gram packet of lyophilized bacteria, such as "Cobactin" from Biotechniques Laboratories, Inc., Redmond, Wash., when added to ten gallons of water, yields 10,000 single-animal doses for cattle.

Alternatively, vessel 20 may be controllably filled with aqueous carrier medium such as water through appropriate valves and plumbing connected to a supply of said medium and entering vessel 20 at a convenient location, such as through cover 152 or from the bottom (not shown).

In either embodiment above, gravimetric scale 61 informs the operator when vessel 20 has been filled with the correct mass of liquid, such as a fresh supply of aqueous carrier medium before a known mass of bacteria is added thereto. The "tare" weight is the mass of all components of apparatus 10, including "empty" vessel 20, that are mounted to frame 160 which rests on loading pan 62. An "empty" vessel 20 may simply have a subthreshold low volume of liquid remaining in it. The "full" weight is equal to the "tare" weight plus the desired mass of liquid contained in vessel 20 and plumbing connected thereto.

Refrigeration means 50 chills the liquid contents of vessel 20 to a temperature preselected by the operator and sensed by thermostat means 70 (generally between 36° and 50° F.). Thermostat means 70 provides the electrical thermal feedback signal via switch 73 and other appropriate electronic circuitry to refrigeration means 50, energizing compressor 52 whenever the temperature of the liquid contained in vessel 20 rises above an operator-preset upper temperature limit, and de-energizing compressor 52 whenever said temperature drops below an operator-preset lower temperature limit. Operator-setting of upper and lower temperature limits may be accomplished via manually adjusting thermostat setpoints at switch 73.

Mixer 80 periodically agitates the concentrated bacterial liquid suspension during storage in vessel 20 to ensure temperature uniformity thereof and to ensure bacterial concentration uniformity. Mixer 80 is also run whenever a fresh batch of concentrated bacterial suspension is being prepared and whenever a portion of the contained volume of concentration bacterial liquid suspension is being dispensed from vessel 20.

The angular velocity of the rotor of mixer motor 81 is governed by motor speed controller 84. Motor 81 runs at a fast speed, as manually preset by control 87, whenever the operator is adding dried bacteria 95 to the liquid contained in vessel 20, to facilitate dispersion. (The operator turns manual control switch 85 on to activate the fast mixing speed. Switch 85 is kept in the off position during all other times.) Motor 81 periodically runs at a medium speed as manually preset by control 88, during storage of concentrated bacterial liquid suspension in vessel 20, to ensure temperature and bacterial concentration uniformity throughout the volume of liquid. A typical period is one minute running every fifteen minutes, as triggered by cycle timer 130 electrically connected to motor speed controller 84 via cable 131. Motor 81 also runs at a medium speed whenever liquid is being dispensed from vessel 20. Motor 81 runs at a slow speed, as manually preset by control 89, whenever refrigeration means 50 is running, to prevent localized freezing of the concentrated bacterial liquid suspension against the walls of vessel 20.

Valves 30 and 120 and pump 40, in combination, drain vessel 20 and recirculate the concentrated bacterial liquid suspension 23 to ensure uniformity of temperature a concentration thereof. Valve 30 and pump 40 are energized simultaneously, allowing flow of liquid from vessel means 20 through flexible hydraulic conduits 33 and 43. When valve 30 and pump 40 are energized, but valve 120 is de-energized, liquid from vessel 20 is pumped from opening 22 through valve 30, conduit 33, pump 40, conduit 43, valve 120 to bypass port 122, through flexible hydraulic conduit 125, and exiting outlet nozzle 127 back into vessel 20, thereby effecting recirculation of the liquid contents of vessel 20.

When valves 30 and 120 and pump 40 are simultaneously energized, liquid from vessel 20 is pumped from opening 22, through valve 30, conduit 33, pump 40, conduit 43, valve 120 to "OUT" port 123, and exiting nozzle 124, thereby effecting dispensation of concentrated bacterial liquid suspension from vessel 20. Because valve 120 is utilized for both dispensing and recirculation functions, as described above, recirculation and dispensation cannot occur simultaneously.

Switched electrical power from cycle timer 130 simultaneously energizes pump 40 and valve 30 for recirculating the contents of vessel 20. The operator presets the durations of energization and non-energization on cycle timer 130, such as a one-minute energization every fifteen minutes.

Simultaneous energization of valves 30 and 120, and of pump 40, for dispensing a portion of the concentrated bacterial liquid suspension from vessel 20 is effected by an electrical signal from CPU 140. If the present apparatus is used in conjunction with a separate weighing and/or metering system 200 (as in U.S. Pat. No. 4,733,971), CPU 140 is also electrically interfaced with the scale means 217 (FIG. 1), and possibly other components of system 200, to achieve an integrated system for feed formulation, preparation and delivery. Alternatively, if the apparatus of the present invention is used alone, simultaneous energization of valves 30 and 120 and pump 40 may be effected by a simpler process controller than a microprocessor, such as a relay or analogous switching device.

FIG. 2 Embodiment

Figure 2:
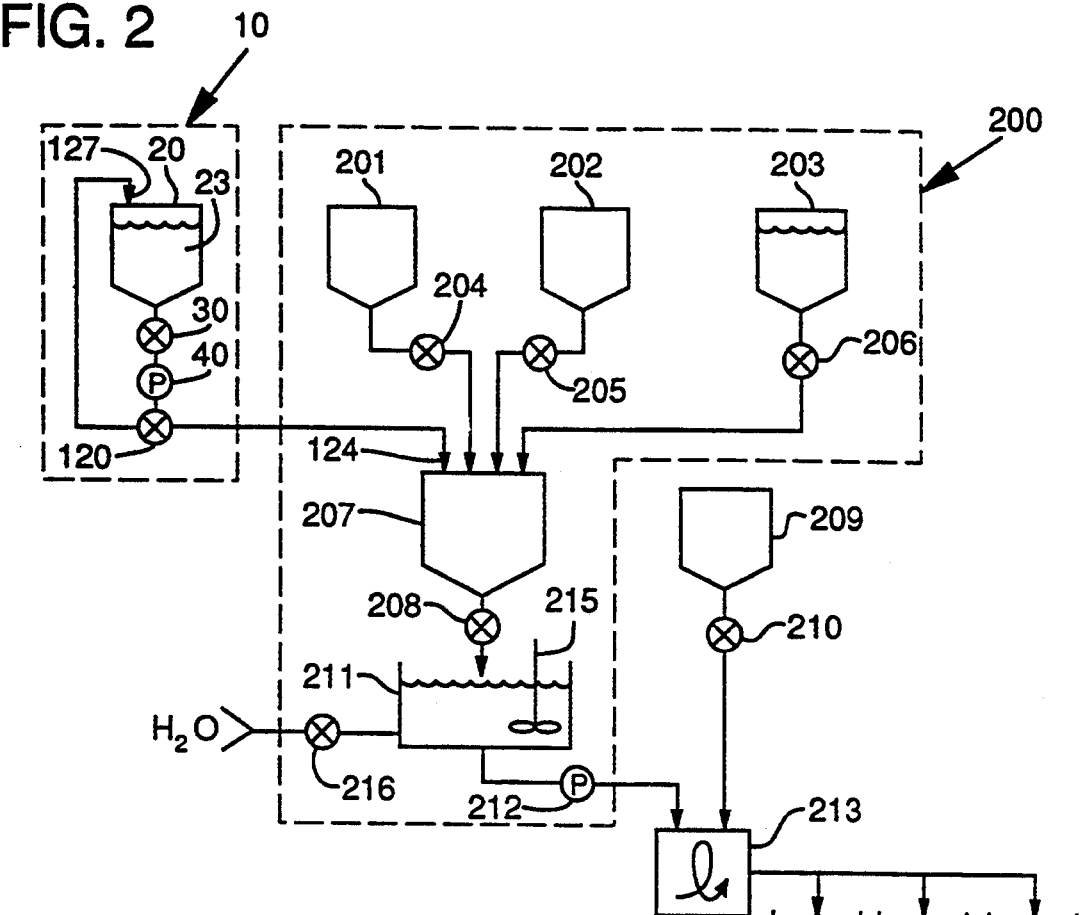
FIG. 2 is a block diagram schematic illustrating use of the present invention together with a separate weighing system (such as disclosed in U.S. Pat. No. 4,733,971) that controllably dispenses microingredient additives, both liquid and dry, into a mixing tank filled with a known volume of water, before mixing the resulting slurry with a known amount of animal feed.

In one embodiment, as shown partially in FIG. 1 and schematically in FIG. 2, concentrated bacterial liquid suspension 23 from apparatus 10 exits nozzle 124 upon simultaneous energization of pump 40 and valves 30 and 120 into a weighing or volumetric metering hopper 207 of separate weighing system 200. Hopper 207 is typically partitioned into separate chambers, one for each of the other microingredients controllably dispensed therein from microingredient containers 201, 202 and 203 through valves 204, 205 and 206, respectively. Alternatively, multiple hoppers can be used. Hopper 207 can either be rotatably tipped to empty its contents (not shown), or the contents can be dumped through a bottom door or drained through valves 208 (one valve 208 for each chamber of hopper 207). Hopper 207 empties into mix tank 211 which has been prefilled with a known volume or mass of carrier water through valve 216, thereby creating a dilute microingredient suspension of known concentration. The dilute suspension is agitated with mixer 215 to achieve a uniform mixture, then drained using pump 212 into feed truck 213 which has been prefilled with a known mass or volume of animal feed from bin 209 through valve 210. As the dilute microingredient suspension is added to the feed in truck 213, the feed is tumbled or otherwise agitated to ensure uniform distribution of suspension throughout the feed. Afterward, the feed is delivered to feed bunks 214 for presentation to the animals.

In the FIG. 2 embodiment, the concentrated liquid suspension of live bacteria simply becomes one of several microingredients available for formulation with other microingredients, upon demand, and selected by a feed truck operator through a remote control terminal (not shown) of CPU 140, adjacent to feed truck 213. That is, the system of FIG. 2 operates essentially as described in U.S. Pat. No. 4,733,971.

FIG. 3 Embodiment

Figure 3:
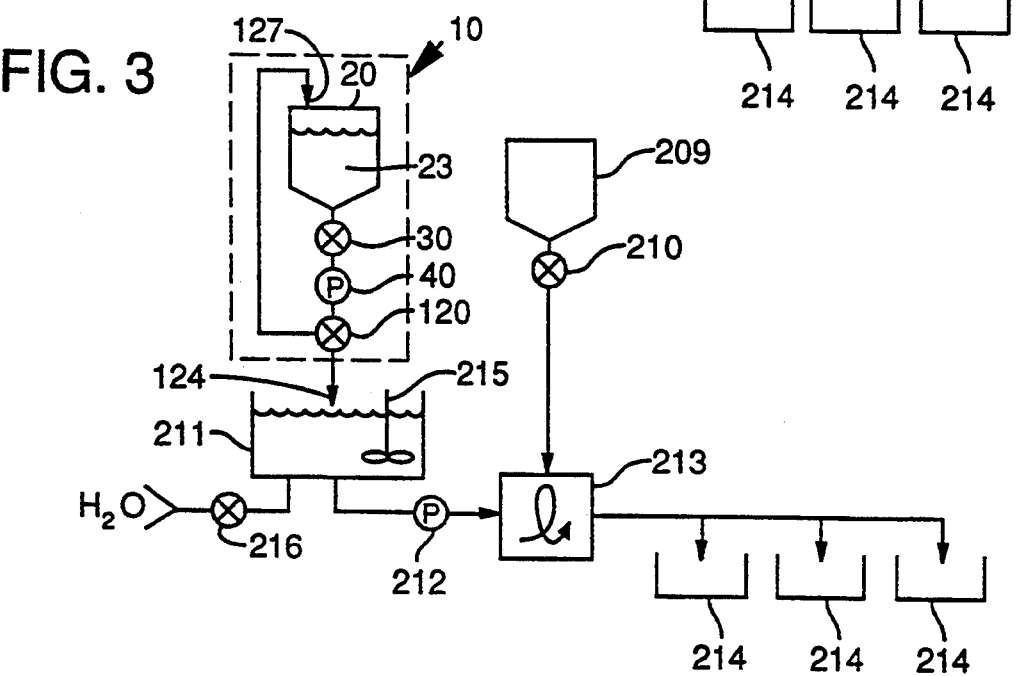
FIG. 3 is a block diagram schematic illustrating use of the present invention with a mixing tank filled with a known volume of water, where a known mass or volume of concentrated bacterial liquid suspension is added to a known mass or volume of water before being added to and mixed with animal feed or before being separately administered to animals as a liquid, such as by drenching.

In a second embodiment, as shown schematically in FIG. 3, concentrated bacterial liquid suspension 23 from apparatus 10, on demand, exits nozzle 124 directly into mix tank 211 prefilled with a known volume or mass of water through valve 216. In this second embodiment, no separate weighing or volumetric metering system is used. Instead, gravimetric scale 61 is used to monitor the dispensation of liquid from vessel 20 (as net weight loss). The addition of a known mass of concentrated bacterial suspension 23 to a known mass or volume of water in mix tank 211 creates a dilute suspension of bacteria at a known, proper dilution. The dilute suspension is agitated with mixer 215 to achieve a uniform mixture, then drained using pump 212 into feed truck 213 which has been prefilled with a known mass or volume of animal feed from bin 209 through valve 210. As the dilute bacterial suspension is added to the feed in truck 213, the feed is tumbled or otherwise agitated to ensure uniform distribution of suspension throughout the feed. Afterward, the feed is delivered to feed bunks 214 for presentation to the animals.

The second embodiment shown in FIG. 3 can also be used to prepare a dilute bacterial suspension for purposes other than adding to animal feed. For example, the dilute suspension in mix tank 211 can be conducted to a drenching apparatus for direct oral administration of therapeutic dosages to animals.

In either of the above first and second embodiments, the entire process, from dispensing concentrated bacterial liquid suspension from apparatus 10 to presentation to the animals for consumption, need consume only a few minutes, which is a sufficiently short amount of time that no significant bacterial death occurs.

The concentration and volume of dilute bacterial suspension contained in mix tank 211 can be carefully tailored to ensure that the entire amount of feed to which the dilute bacterial suspension is added is uniformly coated wih bacteria without wasting excess liquid. Further, the concentration of bacteria in the dilute suspension contained in mix tank 211 can be carefully tailored to such variables as the total mass or volume of feed, average feed granule size, particle density, and surface area, and amount of feed normally consumed by each animal at a single feeding, to optimize the bacterial dosage each animal receives at a feeding.

Both the system of FIG. 2 and that of FIG. 3 are capable of delivering small, accurate dosages of live bacteria in liquid suspension on a regular basis and on demand to large numbers of livestock, such as cattle in commerical feedlots, when the concentrated suspension is first diluted with an aqueous liquid carrier and then intermixed with the animals' feed rations.

Having illustrated and described the principles of the invention in a principal and several alternative embodiments, it should be apparent to those skilled in the art that the invention can be modified in arrangement and detail without departing from such principles. I claim all modifications coming within the spirit and scope of the following claims.

I claim:

1. An apparatus for maintaining live probiotic bacteria at an animal feedlot in a ready-to-administer condition for administration as a feed additive for animals at the feedlot, the apparatus comprising:
   (a) liquid holding means for containing an amount of a suspension of live probiotic bacteria in a carrier liquid;
   (b) cooling means associated with said liquid holding means for cooling the suspension in said liquid holding means;
   (c) agitation means for agitating the suspension in said liquid holding means to achieve and maintain uniformity of the suspension in said liquid holding means;
   (d) delivery means for delivering at least a portion of the suspension from said liquid holding means on demand;
   (e) measurement means for determining an amount of the suspension contained in said liquid holding means; and
   (f) control means operable to
   operate said agitation means when probiotic bacteria are added to the carrier liquid in said liquid holding means so as to achieve uniformity of the suspension in said liquid holding means;
   operate said agitation means to maintain uniformity of the suspension in said liquid holding means; and
   operate said cooling means in response to changing temperatures of the suspension in said liquid holding means so as to maintain a temperature of the suspension in said liquid holding means within a predetermined temperature range such that a predetermined concentration of probiotic bacteria is maintained in the suspension in said liquid holding means without substantial propagation of the bacteria and without substantial loss of viability of the bacteria.

2. An apparatus as recited in claim 1 wherein said agitation means includes recirculation means for recirculating the liquid suspension.

3. An apparatus as recited in claim 1 wherein said measurement means comprises a gravimetric scale supporting said liquid holding means.

4. An apparatus as recited in claim 1 wherein said control means comprises a cycle timer.

5. An apparatus as recited in claim 2 wherein said delivery means and said recirculation means include a common discharge conduit from said liquid holding means and a three-way valve hydraulically coupled to the common discharge conduit, the three-way valve operable by said control means for controlling recirculation and delivery of the suspension.

6. An apparatus as recited in claim 5 wherein said delivery means and said recirculation means include a pump hydraulically coupled to the common discharge conduit, the pump operable by said control means for controllably recirculating and dispensing suspension from said liquid holding means.

7. An apparatus as recited in claim 1 wherein said liquid holding means further comprises a cover for enclosing said liquid holding means and a closable access opening in the cover for adding a quantity of probiotic bacteria to said liquid holding means for intermixing with the carrier liquid.

8. An apparatus as recited in claim 2 wherein said measurement means comprises a gravimetric scale supporting said liquid holding means.

9. An apparatus for maintaining live probiotic bacteria at an animal feedlot in a ready-to-administer condition for administration as a feed additive to animals at the feedlot, the apparatus comprising:
   (a) a first vessel for receiving a first aqueous carrier liquid and a quantity of probiotic bacteria;
   (b) first agitation means for agitating the liquid in the first vessel to form and maintain a first uniform suspension of the bacteria and liquid at a known first concentration in the first vessel;
   (c) cooling means associated with the first vessel for cooling the first suspension in the vessel;
   (d) first delivery means for delivering the first suspension from the first vessel;
   (e) a second vessel for receiving the first suspension delivered from the first vessel;
   (f) means for delivering a second aqueous carrier liquid to the second vessel for intermixing with the first suspension in the second vessel;
   (g) second agitation means for agitating the first suspension and the second carrier liquid in the second vessel to form and maintain a second uniform suspension comprising the first suspension and the second carrier liquid in the second vessel such that the second suspension has a known second concentration of probiotic bacteria that is less than the first concentration of probiotic bacteria in the first suspension;
   (h) second delivery means for delivering the second suspension from the second vessel; and
   (i) control means operable to
   operate the first agitation means to form and maintain the first suspension in the first vessel;
   operate said cooling means so as to maintain the temperature of the first suspension within a predetermined temperature range such that the predetermined first concentration of probiotic bacteria is maintained in the first suspension without substantial propagation and without substantial loss of viability of the probiotic bacteria;
   on demand, operate said first delivery means to deliver a demanded amount of the first suspension from the first vessel into the second vessel;
   while the first suspension is in the second vessel, operate the second agitation means in the second vessel to form and maintain the second suspension within the second vessel; and
   after the second suspension is formed in the second vessel, operate the second delivery means to deliver the second suspension from the second vessel to a receiving station for intermixing the delivered second suspension with a feed ration.

10. An apparatus as recited in claim 9 further comprising first measurement means for determining an amount of the first suspension contained in the first vessel.

11. An apparatus as recited in claim 10 further comprising second measurement means for determining an amount of the second suspension contained in the second vessel.

12. An apparatus as recited in claim 9 including multiple feed additive storage means including the first vessel and at least one additional additive storage means, wherein each additional additive storage means has associated therewith a corresponding additive delivery means for delivering the corresponding feed additive from the corresponding additive storage means to the second vessel, said control means being also operable to operate each corresponding additive delivery means on demand so as to form the second suspension, containing the first suspension together with the other feed additives delivered from said additional additive storage means, for delivery to and intermixing with a feed ration for a population of animals.

* * * * *